(12) United States Patent
Anderson

(10) Patent No.: US 10,071,223 B2
(45) Date of Patent: Sep. 11, 2018

(54) COMPRESSION RESISTANT HOSE

(71) Applicant: Edwards Lifesciences Corporation, Irvine, CA (US)

(72) Inventor: Daniel C. Anderson, Brea, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 312 days.

(21) Appl. No.: 14/931,630

(22) Filed: Nov. 3, 2015

(65) Prior Publication Data

US 2016/0121078 A1  May 5, 2016

Related U.S. Application Data

(60) Provisional application No. 62/075,383, filed on Nov. 5, 2014.

(51) Int. Cl.
*A61M 25/00* (2006.01)

(52) U.S. Cl.
CPC ....... *A61M 25/005* (2013.01); *A61M 25/0045* (2013.01)

(58) Field of Classification Search
CPC ............ A61M 25/005; A61M 25/0045; A61M 25/10; A61M 25/0012; F16L 11/082; F16L 11/118; A61B 1/122
USPC .......................... 604/524–527; 138/123–134
See application file for complete search history.

(56) References Cited

U.S. PATENT DOCUMENTS

| | | | |
|---|---|---|---|
| 4,203,476 A | 5/1980 | Vitellaro | |
| 5,470,322 A | 11/1995 | Horzewski et al. | |
| 8,142,415 B2 | 3/2012 | Warnock, Jr. et al. | |
| 9,095,286 B2 * | 8/2015 | Vazales | A61B 1/122 |
| 2004/0153049 A1 * | 8/2004 | Hewitt | A61M 25/0012 604/527 |
| 2005/0107738 A1 * | 5/2005 | Slater | A61M 25/10 604/96.01 |
| 2007/0267785 A1 * | 11/2007 | Bellamy | B29C 65/10 264/512 |
| 2009/0320951 A1 * | 12/2009 | Witz | F16L 11/082 138/125 |
| 2014/0130930 A1 * | 5/2014 | Ragner | F16L 11/118 138/121 |

FOREIGN PATENT DOCUMENTS

WO  2005072806 A2  8/2005

* cited by examiner

*Primary Examiner* — Manuel Mendez

(57) ABSTRACT

Described herein is a hose, wherein the hose has a length having a distal end and a proximal end, and an inner diameter and an outer diameter. The hose is comprised of a first layer; and a second layer, wherein the first layer and the second layer extend along at least a portion of the length and wherein a longitudinal compressive force applied to either the distal end or the proximal end of the hose causes the first layer to lock against the second layer.

18 Claims, 8 Drawing Sheets

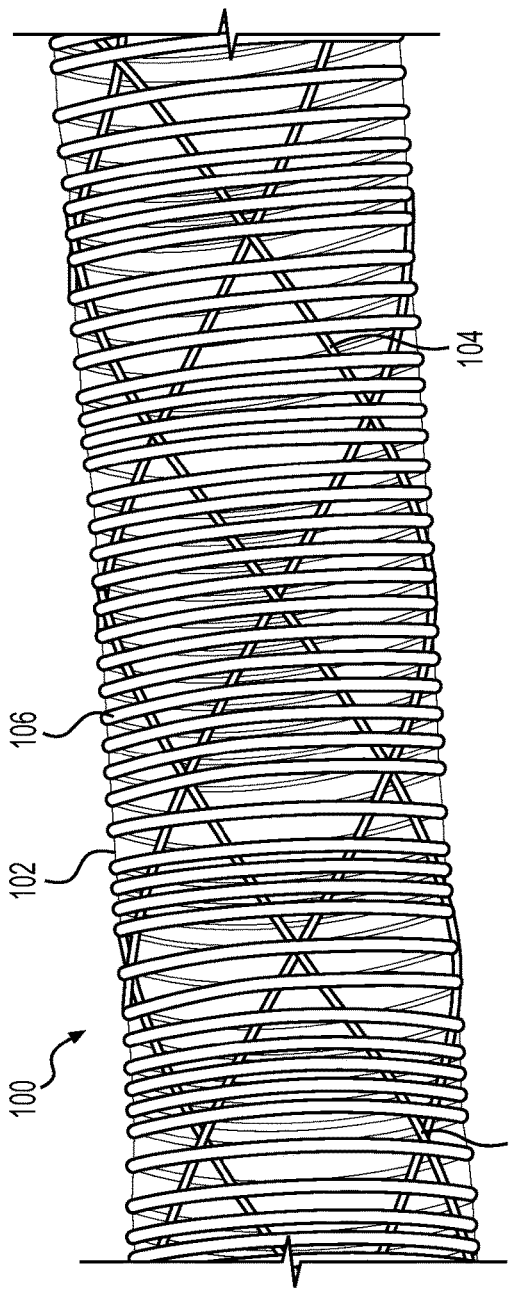
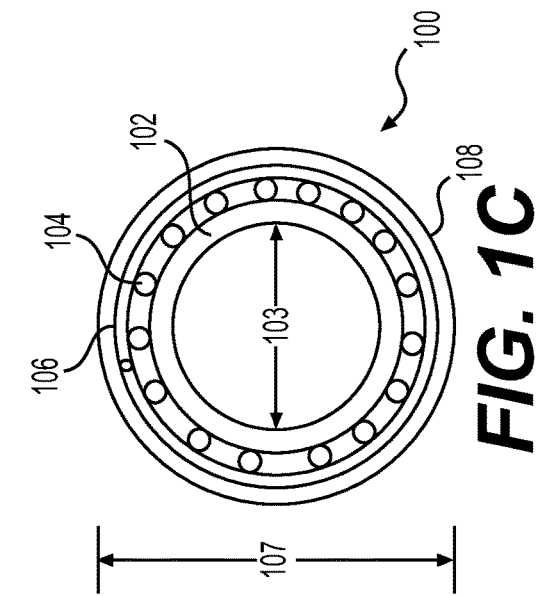
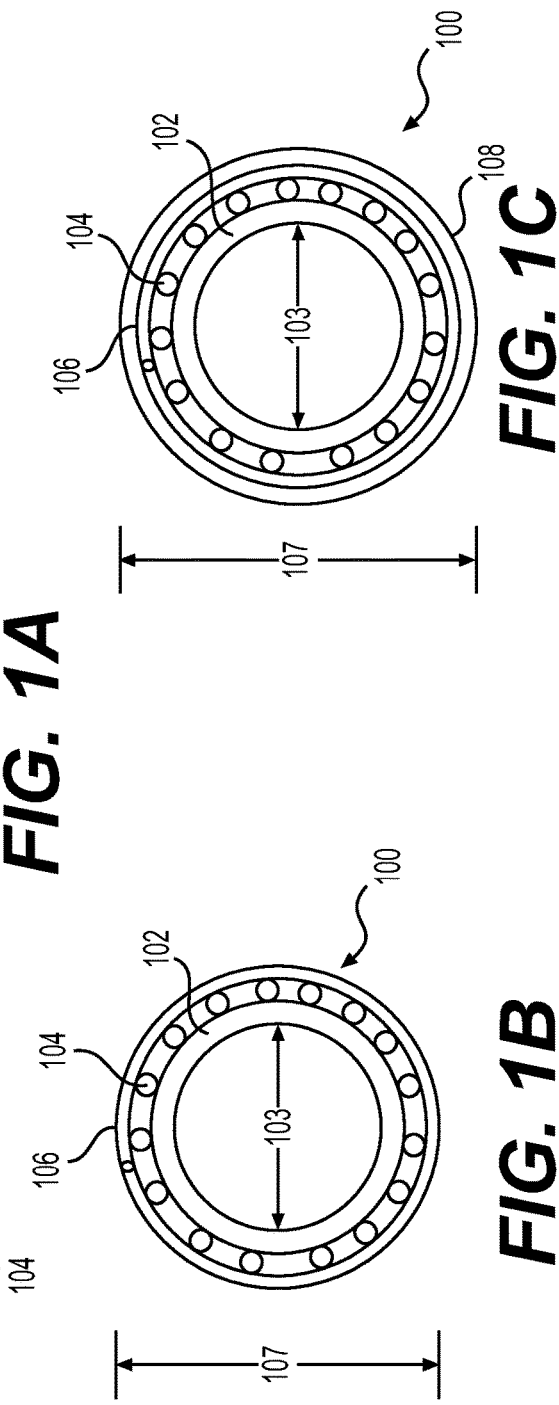

COMPRESSION RESISTANT HOSE

RELATED APPLICATIONS

This application claims the benefit of priority to U.S. Provisional Application No. 62/075,383, filed Nov. 5, 2014, which is hereby incorporated by reference in its entirety for all purposes.

TECHNICAL FIELD

This application relates to methods, systems, and apparatuses for hoses, more specifically to hoses used in applications that may create a compressive load oriented axially along the length of the hose, and more specifically to medical applications of hoses in those situations. Further, the invention relates to those applications where the body of the hose is subject to creep, and more specifically, creep in a long-term implantable hose.

BACKGROUND

Hoses have been reinforced in various ways for many different applications. These reinforcements can include braids on the outside of hoses for abrasion resistance, braids for mechanical reinforcement against the hose's internal pressure load (such as that created by a fluid under high pressure), coils or convolutions for crush resistance (i.e., kinking or transverse compression), and coils or braids for strain relief near junctions, among others. Generally, these reinforcements are intended to protect the hose from internal pressures, external radial loads (crushing, bending, or kinking) and tensile forces (anti-stretch). In other instances, metallic tubes such as those comprised of nickel-titanium alloy (nitinol) have been used, but these tubes lack the flexibility desired for certain applications and must be laser cut for the specific uses.

Polymer hoses are flexible and can be easily dimensioned for medical implant applications; however, the reinforcements described above are not meant to guard against longitudinal compression loads on the hose. This longitudinal compression may cause compressive creep of the hose, which can present challenges in applications requiring high-accuracy that is maintained over time such as a long-term medical implant. For example, a hose or tube may be used to precisely position a medical device in a patient. The hose can be implanted over a separate flexible guide shaft and anchored at one end. The medical device may be attached to the hose at the other end. Loads on the medical device (e.g., heart beats of the patient) can cause axially compressive loading of the hose, which can lead to compressive creep of the hose and lead to loss of accurate positioning of the medical device within the patient. Tests have shown that methods of reinforcing with coil or braid alone do not provide significant creep resistance when loaded in a manner representative of this application.

Therefore, devices, systems, apparatus, and methods are needed that overcome challenges in the art. Specifically, devices, systems, apparatus, and methods are needed that resist compressive creep of a hose caused by axially compressive loads.

SUMMARY

The present invention is directed to embodiments of a compression resistant hose and applications of such a hose. An aspect of the present disclosure is directed to a hose. The hose has a length having a distal end and a proximal end, and an inner diameter and an outer diameter. The hose comprises a first layer that forms the inner diameter; a second layer that can be braided or coiled substantially about the first layer, wherein the second layer extends along at least a portion of the length; and a third helically coiled layer substantially about the second layer, wherein the third helically coiled layer extends along at least a portion of the length.

Alternatively or optionally, the hose may comprise a fourth layer substantially about the helically coiled layer. The fourth layer may form the outer diameter.

The hose is configured to minimize longitudinal compression creep caused by a force applied to either the distal or proximal end. A longitudinal compressive force applied to the hose causes the braided layer to lock against the helically coiled layer. The braided layer may comprise a wire braided layer. The wire braided layer may be comprised of round wire. The round wire that comprises the wire braided layer may have a diameter of 0.003".

Alternatively or optionally, the wire braided layer may be comprised of flat wire. Also alternatively or optionally, the wire braided layer may be comprised of round wire and flat wire. The flat wire that comprises the wire braided layer may have dimensions of 0.001"×0.003". The wire braided layer may be comprised of alloy wire. The alloy wire that comprises the wire braided layer may be 316L stainless steel wire. The helically coiled layer about the braided layer may comprise a wire helically coiled layer about the braided layer. The wire helically coiled layer about the braided layer may be comprised of round wire. The round wire that comprises the wire helically coiled layer about the braided layer may have a diameter of 0.003".

Alternatively or optionally, the wire helically coiled layer about the braided layer may be comprised of flat wire. Also alternatively or optionally, the wire helically coiled layer about the braided layer may be comprised of round wire and flat wire. The flat wire that comprises the wire helically coiled layer about the braided layer may have dimensions of 0.001"×0.003" to 0.001"×0.005". The wire helically coiled layer about the braided layer may be comprised of alloy wire. The alloy that comprises the wire coiled layer about the braided layer may be comprised of 316L stainless steel wire.

The braided layer may be comprised of a long-pitch braided layer. The long-pitch braided layer may have a pitch of between and including 1 and 25 picks per inch (ppi). The long-pitch braided layer may have a pitch of between and including 5 and 20 picks per inch (ppi). The pitch of the long-pitch braided layer may vary along the length of the hose.

The helically coiled layer about the braided layer may comprise a short-pitch helically coiled layer about the braided layer. The short-pitch helically coiled layer about the braided layer may have a pitch of between and including 0.005" and 0.050". The short-pitch helically coiled layer about the braided layer may have a pitch of between and including between 0.008" and 0.048". The pitch of the short-pitch helically coiled layer about the braided layer may vary along the length of the hose.

The first layer of the hose may be comprised of a polymer. The composition of the polymer that comprises the first layer may vary along the length of the hose. The fourth layer of the hose may be comprised of a polymer. The composition of the polymer that comprises the fourth layer may vary along the length of the hose. The hose may comprise a fifth layer, wherein the fifth layer is located between the second layer braided substantially about the first layer and the third helically coiled layer. The fifth layer may comprise a polymer. The polymer that comprises the fifth layer may have a density greater than the polymer that comprises the first layer and the polymer that comprises the fourth layer. The composition of the polymer that comprises the fifth layer may vary along the length of the hose. The second layer braided substantially about the first layer may be comprised of ultra-high-molecular-weight polyethylene, glass fiber, carbon fiber, or similar materials. The third helically coiled layer substantially about the braided layer may be comprised of ultra-high-molecular-weight polyethylene, glass fiber, carbon fiber, or similar materials.

The hose may be used for medical applications. For example, the hose may be used to position a medical device within a body. The hose may have a length of between 1 and 900 mm. The hose may have a length of 850 mm. The inner diameter of the hose may vary along its length. The hose may have an inner diameter of less than or equal to 2 mm. The hose may have an inner diameter of 1.91 mm. The outer diameter of the hose may vary along its length. The hose may have an outer diameter of less than or equal to 5 mm. The hose may have has an outer diameter of 2.41 mm.

Another aspect of the present invention comprises a hose having a length, a distal end, a proximal end, an inner diameter and an outer diameter. This embodiment of a hose comprises a first layer and a second layer. The first layer and the second layer extend along at least a portion of the length and the first layer locks against the second layer when a longitudinal compressive force is applied to either the distal end or the proximal end of the hose.

Alternatively or optionally, the first layer can comprise a braided layer such a, for example, a wire braided layer and the second layer can comprise a helically coiled layer such as, for example, a wire helically coiled layer.

Alternatively or optionally, the first layer can comprise a helically coiled layer and the second layer can comprise a helically coiled layer, wherein the helically coiled layer of the second layer is wrapped in a direction opposite the helically coiled layer of the first layer.

The hose can also comprise one or more additional layers and in various embodiments the one or more additional layers can form one or more of inner and outer diameters of the hose.

Another aspect comprises a method of positioning a medical device in a patient using a hose. The method comprises implanting the hose over a separate flexible guideshaft, which is itself anchored at a distal location; anchoring the hose at its proximal end; and attaching a medical device to the hose at its distal end, wherein the hose is comprised of a first layer that forms the inner diameter; a second layer braided substantially about the first layer, wherein the second braided layer extends along at least a portion of the length; and a third helically coiled layer substantially about the braided layer, wherein the a third helically coiled layer extends along at least a portion of the length. The hose is configured to minimize longitudinal compression creep caused by a force applied to either the distal end or the proximal end of the hose. A longitudinal compressive force applied to either the distal end or the proximal end of the hose causes the braided layer to lock against the helically coiled layer, preventing further compression of the hose and thereby preventing further movement of the medical device. The braided layer of the hose may comprise a long-pitch braided layer. The helically coiled layer about the braided layer of the hose may comprise a short-pitch helically coiled layer about the braided layer.

BRIEF DESCRIPTION OF THE DRAWINGS

The device is explained in even greater detail in the following drawings. The drawings are merely examples to illustrate the structure of preferred devices and certain features that may be used singularly or in combination with other features. The invention should not be limited to the examples shown.

FIG. 1A is a photograph of a section of a hose according to an embodiment of the present invention;

FIG. 1B is an axial view of the embodiment of a hose as shown in FIG. 1A;

FIG. 1C illustrates an embodiment of a hose further comprising a fourth layer substantially about the helically coiled layer;

DETAILED DESCRIPTION

Figure 1D:
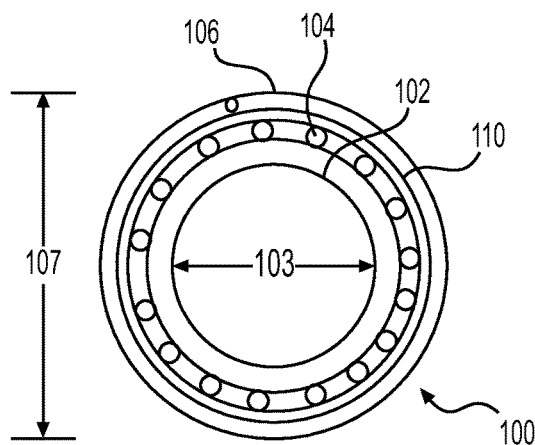
FIG. 1D illustrates yet another embodiment of a hose further comprising a fifth layer located between the second layer braided substantially about the first layer and the third helically coiled layer.

Implementations of the present disclosure are described more fully hereinafter. Indeed, these implementations can be embodied in many different forms and should not be construed as limited to the implementations set forth herein; rather, these implementations are provided so that this disclosure will satisfy applicable legal requirements.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. The term "comprising" and variations thereof as used herein is used synonymously with the term "including" and variations thereof and are open, non-limiting terms. "Exemplary" means "an example of" and is not intended to convey an indication of a preferred or ideal embodiment. "Such as" is not used in a restrictive sense, but for explanatory purposes. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description. In general, such embodiments relate to embodiments of a compression resistant hose and applications of such a hose.

FIG. 1A is a photograph of a section of a hose according to an embodiment of the present invention. The hose 100 has a length having a distal end and a proximal end, an inner diameter and an outer diameter. As can be seen in FIG. 1A, the hose is comprised of a first layer 102 that forms the inner diameter; a second layer 104 substantially about the first layer 102, wherein the second layer 104 extends along at least a portion of the length of the hose 100. In one embodiment, the second layer is a braided layer. In another embodiment, the second layer is a helically coiled layer wrapped in a direction opposite the helically coiled layer of the third layer.

FIG. 1B is an axial view of the embodiment of a hose as shown in FIG. 1A. The embodiment of FIG. 1B is comprised of a hose 100 having a distal end and a proximal end, an inner diameter 103 and an outer diameter 107. In this embodiment, the hose comprises a first layer 102 that forms the inner diameter 103. Further comprising this embodiment is a second layer 104 that can be braided substantially about the first layer 102. In this embodiment, the second braided layer 104 extends along at least a portion of the length of the hose. This embodiment further comprises a third helically coiled layer 106 substantially about the braided layer 104, wherein the third helically coiled layer 106 also extends along at least a portion of the length of the hose 100.

When a compressive force is applied to the hose 100 at either the distal or proximal ends of the hose 100 or along at least a portion of its length, the second braided layer 104 expands radially. However, when the second braided layer 104 expands, it encounters the third helically coiled layer 106, which locks the second braided layer 104 in place and prevents further radial expansion. This provides a stiffness to the hose 100 that minimizes longitudinal compression creep caused by a force applied to either the distal or proximal ends of the hose 102 or a force that may be applied along at least a portion of the length of the hose 100 that results in a longitudinal compressive force.

As described herein, the hose 100 comprises a first layer 102 that forms the inner diameter 103. Generally, the first layer 102 is comprised of a polymer, but it is to be appreciated that it may be comprised of any suitable material such as rubber, vinyl, and the like. As a non-limiting example, the first layer 102 may be comprised of a biocompatible polymer such as Carbothane™ (The Lubrizol Corporation, Wickliffe, Ohio), Bionate™ (DSM Biomedical Inc, Berkley, Calif.), and the like. In some embodiments, the composition of the polymer that comprises the first layer can vary along the length of the hose, or the first layer 102 can be comprised of layers of polymer having different compositions. In one embodiment, the hose 100 can have an inner diameter 103 of less than or equal to 2 mm. For a non-limiting example, the hose 100 can have an inner diameter 103 of 1.91 mm. In another aspect, the inner diameter 103 of the hose can vary along its length. In one embodiment, the hose 100 can have an outer diameter 107 of less than or equal to 5 mm. For a non-limiting example, the hose 100 can have an outer diameter 107 of 1.91 mm. In one aspect, the outer diameter 107 of the hose 100 can vary along its length.

In yet another embodiment, the hose 100 can be comprised of a first layer 102 and a second layer 104. The first layer 102 and the second layer 104 extend along at least a portion of the length and the first layer locks 102 against the second layer 104 when a longitudinal compressive force is applied to either the distal end or the proximal end of the hose 100. For example, as shown in FIG. 1E, the first layer 102 can comprise a braided layer such as, for example, a wire braided layer and the second layer 104 can comprise a helically coiled layer such as, for example, a wire helically coiled layer. Alternatively or optionally, as shown in FIG. 1F, the first layer 102 can comprise a helically coiled layer and the second layer 104 can comprise a helically coiled layer, wherein the helically coiled layer of the second layer 102 is wrapped in a direction opposite the helically coiled layer 104 of the first layer.

Figure 1E:
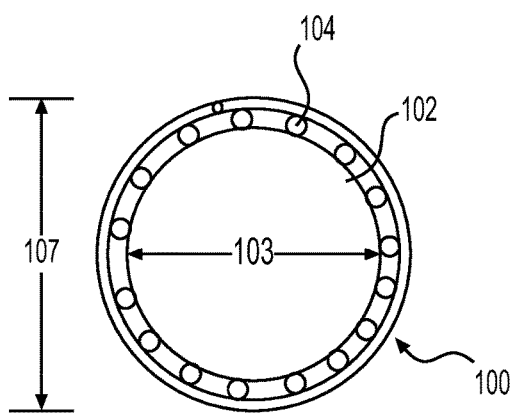
FIG. 1E illustrates an embodiment of a hose comprising a braided first layer and a helically coiled second layer.
Figure 1F:
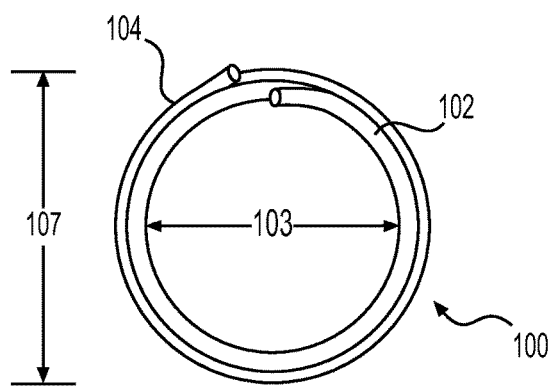
FIG. 1F illustrates an embodiment of a hose comprising a helically coiled first layer and a helically coiled second layer.

Though not shown in FIG. 1E or 1F, the hose can further comprise one or more additional layers. For example, at least one of the one or more additional layers forms an inner diameter of the hose or at least one of the one or more additional layers forms an outer diameter of the hose. Any one of the one or more additional layers can be comprised of a polymer.

Figure 2:
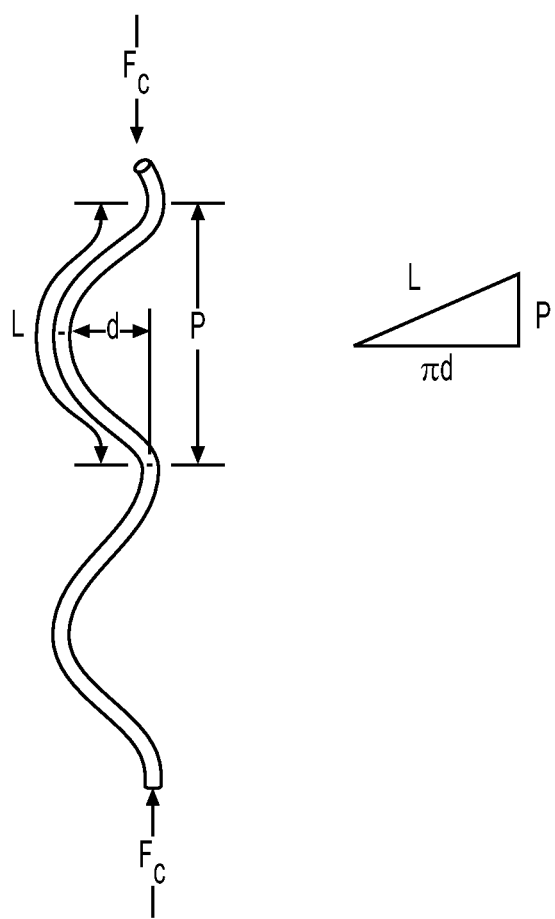
FIG. 2 illustrates the expansion that occurs in a helix when compressed axially by a strain, $\varepsilon$, which is caused by an axial compressive force, $F_c$.

FIG. 2 illustrates the expansion of a helical wire (from either the braided layer 104 or the coiled layer 106) caused by axial compressive force, $F_c$. In FIG. 2, helical wire has a diameter, d, and a pitch, p. Pitch is defined as the axial in-line distance between a consecutive turns of the helical wire. The length of wire, L, is modeled as a hypotenuse of a right triangle with base of ($\Pi$d) and a height of p. Therefore, in a single turn of wire, L is given by:

$$L=\sqrt{p^2+\pi^2 d^2}$$

An axial compressive force, $F_c$, applied at either the distal or proximal ends of the hose 100 or along at least a portion of its length, results in a small change in length, $\varepsilon$, per unit length of the affected segment of hose. This results in a change in pitch from p to p', which is given by the equation:

$$p'=p(1-\varepsilon)$$

and a change of the diameter of the second braided layer 104 from d to d', which is given by the equation:

$$d' = \frac{\sqrt{L^2 - p^2 * (1 - \varepsilon)^2}}{\pi}.$$

Table I, below, illustrates examples of the diameter growth of the helical wire from d to d' when the helical wire has different pitches and an axially compressive strain, ε, of 2% is applied at either the distal or proximal ends of the hose 100.

TABLE I

|  | d in | p in | L in | ε % | Diameter Growth % |
|---|---|---|---|---|---|
| Nominal | 0.08 | 0.05 | 0.256253 | 2% | 0.08% |
| Strained | 0.080063 | 0.049 | 0.256253 |  |  |
| Nominal | 0.08 | 0.1 | 0.270491 | 2% | 0.31% |
| Strained | 0.08025 | 0.098 | 0.270491 |  |  |
| Nominal | 0.08 | 0.25 | 0.354493 | 2% | 1.94% |
| Strained | 0.081552 | 0.245 | 0.354493 |  |  |
| Nominal | 0.08 | 0.5 | 0.559612 | 2% | 7.55% |
| Strained | 0.086041 | 0.49 | 0.559612 |  |  |

As indicated by these results, the coil layer—which has a much smaller pitch than the braided layer—will experience an insignificant amount of diametrical expansion compared to the braided layer. The expansion of the second braided layer 104 causes the braided layer 104 to lock against the helically coiled layer 106. Generally, embodiments of the device 100 work for any combination of inner layer 104 and outer layer 106 pitches that satisfies the following conditions: (a) The pitch of the inner (braided) layer 104 should be substantially greater than that of the outer layer 106; (b) The pitch of the outer (helical) layer 106 should be small enough that the gaps between consecutive turns is small, such that buckling of the inner layer of wires between these turns due to the compressive loading is prevented; and (c) Ideally, the outer layer of reinforcement, the coil 106, has a helix angle (defined as the angle between the wire and the longitudinal axis of the hose) approaching 90 degrees, although the helix angle could be less than this, for example, to allow a desired amount of creep to occur before the locking interference between the wire layers becomes effective.

Referring back to FIGS. 1A-1B, in one embodiment the braided layer 104 comprises a wire braided layer. In one aspect, the wire braided layer can be comprised of round wire. For one non-limiting example, the braided layer 104 can be formed of round wire that has a diameter of approximately 0.003". In another aspect, the wire braided layer can be comprised of flat wire. In yet another aspect, the wire braided layer can be comprised of round wire and flat wire. As a non-limiting example, the flat wire that comprises the wire braided layer can have dimensions of approximately 0.001"×0.003". In various embodiments, the wire braided layer can be comprised of alloy wire such as, for example, 316L stainless steel wire. In other embodiments, the second layer 104 braided substantially about the first layer 102 can be comprised of other materials such as ultra-high-molecular-weight polyethylene, glass fiber, carbon fiber, other alloys, and the like. Generally, the braided layer 104 comprises a long-pitch braided layer. For one non-limiting example, the long-pitch braided layer 104 can have a pitch of between and including 1 and 25 picks per inch (ppi). In another non-limiting example, the long-pitch braided layer 104 can have a pitch of between and including 5 and 20 picks per inch (ppi). In one aspect, the pitch of the long-pitch braided layer can vary along the length of the hose.

In one embodiment, the helically coiled layer 106 about the braided layer 104 comprises a wire helically coiled layer about the braided layer 104. In one aspect, the wire helically coiled layer about the braided layer 104 can be comprised of round wire. As one non-limiting example, the round wire that comprises the wire helically coiled layer about the braided layer 104 can have a diameter of approximately 0.003". In another aspect, the wire helically coiled layer about the braided layer 104 can be comprised of flat wire. In yet another aspect, the wire helically coiled layer about the braided layer 104 can be comprised of round wire and flat wire. Consider as a non-limiting example, the flat wire that comprises the wire helically coiled layer about the braided layer 104 can have dimensions of approximately 0.001"× 0.003" to 0.001"×0.005". In various embodiments, the wire helically coiled layer 106 about the braided layer 104 can be comprised of alloy wire such as, for example, 316L stainless steel wire. In other embodiments, the third helically coiled layer 106 substantially about the braided layer 104 can be comprised of other materials such as ultra-high-molecular-weight polyethylene, glass fiber, carbon fiber, other alloys, and the like. Generally, the helically coiled layer 106 about the braided layer 104 comprises a short-pitch helically coiled layer about the braided layer 104. For one non-limiting example, the short-pitch helically coiled layer 106 about the braided layer 104 can have a pitch of about 0.005". In one embodiment, the pitch of the short-pitch helically coiled layer 106 about the braided layer 104 varies along the length of the hose. In one embodiment, the short-pitch helically coiled layer 106 about the braided layer 104 can form the outer diameter 107 of the hose 100.

FIG. 1C illustrates an embodiment of a hose 100 further comprising a fourth layer 108 substantially about the helically coiled layer. In one aspect, the fourth layer 108 can form the outer diameter 107 of the hose 100. Generally, the fourth layer 108 is comprised of a polymer, but it is to be appreciated that it may be comprised of any suitable material such as rubber, vinyl, and the like. As a non-limiting example, the fourth layer 108 may be comprised of a biocompatible polymer such as Carbothane™ (The Lubrizol Corporation, Wickliffe, Ohio), Bionate™ (DSM Biomedical Inc, Berkley, Calif.), and the like. In some embodiments, the composition of the polymer that comprises the fourth layer 108 can vary along the length of the hose 100, or the fourth layer 108 can itself be comprised of layers of polymer having different compositions.

FIG. 1D illustrates yet another embodiment of a hose 100 further comprising a fifth layer 110 located between the second layer 104 braided substantially about the first layer and the third helically coiled layer 106. This fifth layer 110 can be added in any of the embodiments shown in FIGS. 1A through 1C. Generally, the fifth layer 110 is comprised of a polymer, but it is to be appreciated that it may be comprised of any suitable material such as rubber, vinyl, and the like. As a non-limiting example, the fifth layer 110 may be comprised of a biocompatible polymer such as Carbothane™ (The Lubrizol Corporation, Wickliffe, Ohio), Bionate™ (DSM Biomedical Inc, Berkley, Calif.), and the like. In one embodiment, the polymer that comprises the fifth layer 110 has a density greater than the polymer that comprises the first layer 102 and the polymer that may comprise the fourth layer 108 (if applicable). In some embodiments, the composition of the polymer that comprises the fifth layer 110 can vary along the length of the hose 100, or the fifth layer 110 can be comprised of layers of polymer having different compositions. This fifth layer 110 can be used such that a desired degree of creep is allowed before the locking mechanism prevents further creep. For example, the density and thickness of the fifth layer 110 could be set so that the second layer 104 braided substantially about the first layer is allowed to expand a desired amount, thereby allowing the hose to compress longitudinally (creep), before the second braided layer 104 locks against the third helically coiled layer 106.

Figure 3:
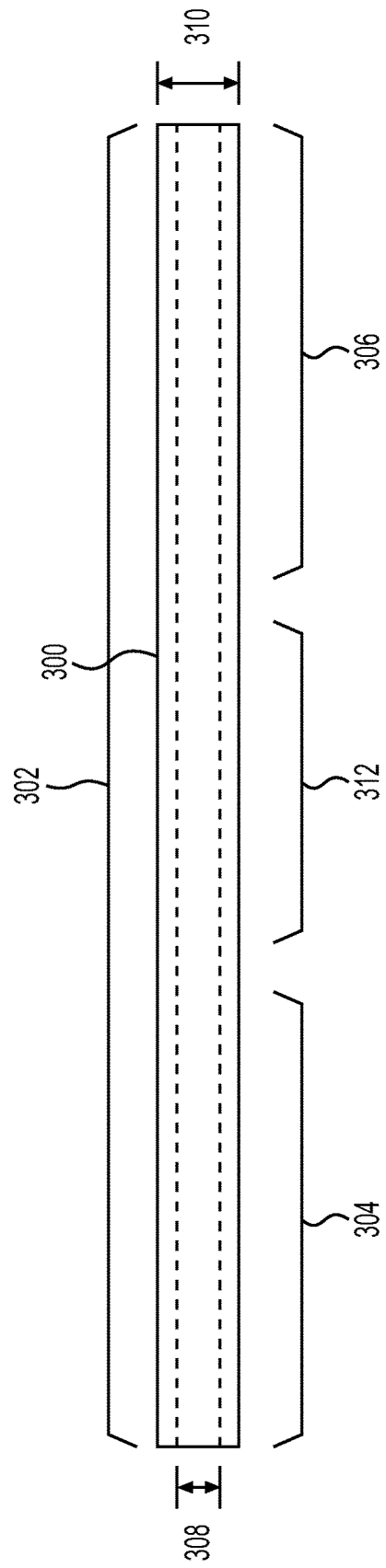
FIG. 3 is a view of an embodiment of a hose according to the present invention.

FIG. 3 is a view of an embodiment of a hose according to the present invention. The hose 300 can have the radial construction as shown in any of FIGS. 1A-1D. As shown in this embodiment, the hose 300 has a length 302. The length 302 can be any desired length. For a non-limiting example, the length 302 may be between approximately 1 and 1000 mm. In one embodiment, the length 302 can be approximately 850 mm. The second braided layer or the third helically coiled layer, as described in reference to FIGS. 1A-1D may not extend the full length 302 of the hose 300. The hose 300 has a distal end 304 and a proximal end 306. As non-limiting examples, the distal end 304 may be approximately 56 mm and the proximal end 306 may be approximately 786 mm. The hose 300 also has an inner diameter 308 and an outer diameter 310. As non-limiting examples, the inner diameter 308 can be approximately 1.91 mm and the outer diameter can be approximately 2.41 mm. Further comprising this embodiment of a hose 300 is a transition section 312. As a non-limiting example, the transition section 312 can be approximately 8 mm. In the transition section 312, one or more of the composition of the layers that form the hose 300, the pitch or composition of the second braided layer, the pitch or composition of the third helically coiled layer, the inner diameter 308 of the hose, the outer diameter 310 of the hose, the radial construction of the hose (for example, from a three-layer hose to a four-layer hose, and the like), or any other parameter of the hose can change. As non-limiting examples, the polymer that comprises one or more layers of the distal section 304 may be comprised of Carbothane™ 72D Aliphatic that transitions to Carbothane™ 55D Aliphatic for the proximal section 306, with the transition occurring in the transition section 312. Similarly, as a non-limiting example, the second braided layer can have a pitch of 5 ppi in the distal end 304 and transition to a pitch of 15-20 ppi in the proximal end 306, with the transition in pitch occurring in the transition section 312. As another non-limiting example, the third helically coiled layer of the hose 300 can have a pitch of approximately 0.048" in the distal end 304 and transition to a pitch of approximately 0.008" or 0.011" in the proximal end 306, with the transition in pitch occurring in the transition section 312.

Figure 4:
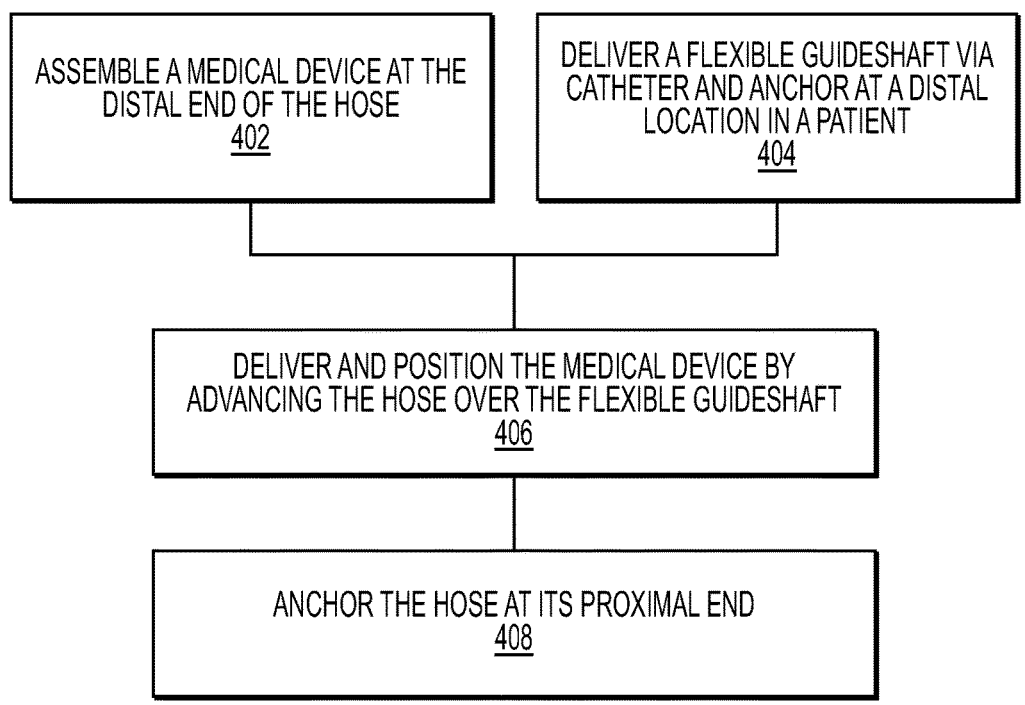
FIG. 4 is an exemplary flowchart that illustrates a method of positioning a medical device in a human or animal using a hose according to embodiments of the present invention.

FIG. 4 is an exemplary flowchart that illustrates a method of positioning a medical device in a human or animal using a hose according to embodiments of the present invention. This embodiment of a method comprises Step 402, in which the medical device is assembled at distal end of hose (e.g., at medical device factory, or attached bedside by physician) and Step 404, in which a flexible guideshaft is delivered via catheter and anchored at distal location in patient. At Step 406, the medical device is delivered and positioned by advancing the hose over the flexible guideshaft. At Step 408, the hose is anchored at the proximal end. The hose is an embodiment of the hose described herein. For example, the hose can be comprised of a first layer that forms the inner diameter; a second layer braided substantially about the first layer, wherein the second braided layer extends along at least a portion of the length; and a third helically coiled layer substantially about the braided layer, wherein the a third helically coiled layer extends along at least a portion of the length. The hose is configured to minimize longitudinal compression creep caused by a longitudinal compressive force applied to either the distal end or proximal end, or along at least a portion of the hose. As described herein, the longitudinal compressive force applied to the distal end or proximal end, or along at least a portion of the hose, causes the braided layer to lock against the helically coiled layer.

Figure 5:
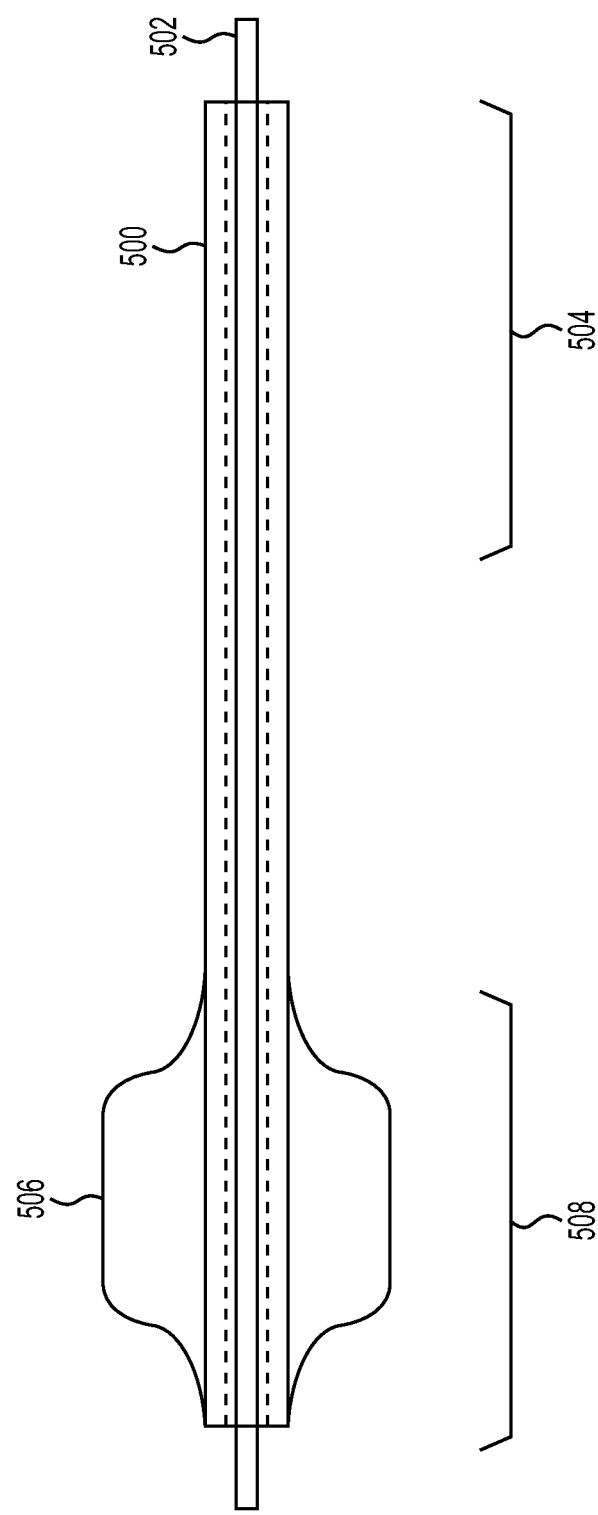
FIG. 5 is an illustration of a system that can be used to practice the method described in FIG. 4.

FIG. 5 is an illustration of a system that can be used to practice the method described in FIG. 4. The system is comprised of a Carbothane™ shaft or hose 500 that is double reinforced by use of a first layer that forms the inner diameter; a second layer braided substantially about the first layer, wherein the second braided layer extends along at least a portion of the length; and a third helically coiled layer substantially about the braided layer. A medical device 506 is attached to the hose 500 at its distal end 508. The hose and medical device assembly 500 and 506 are implanted over a separate flexible guideshaft 502. The hose 500 is anchored at its proximal end 504. For example, a balloon filled with foam can be attached to the distal end 508 of the hose 500.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 6:
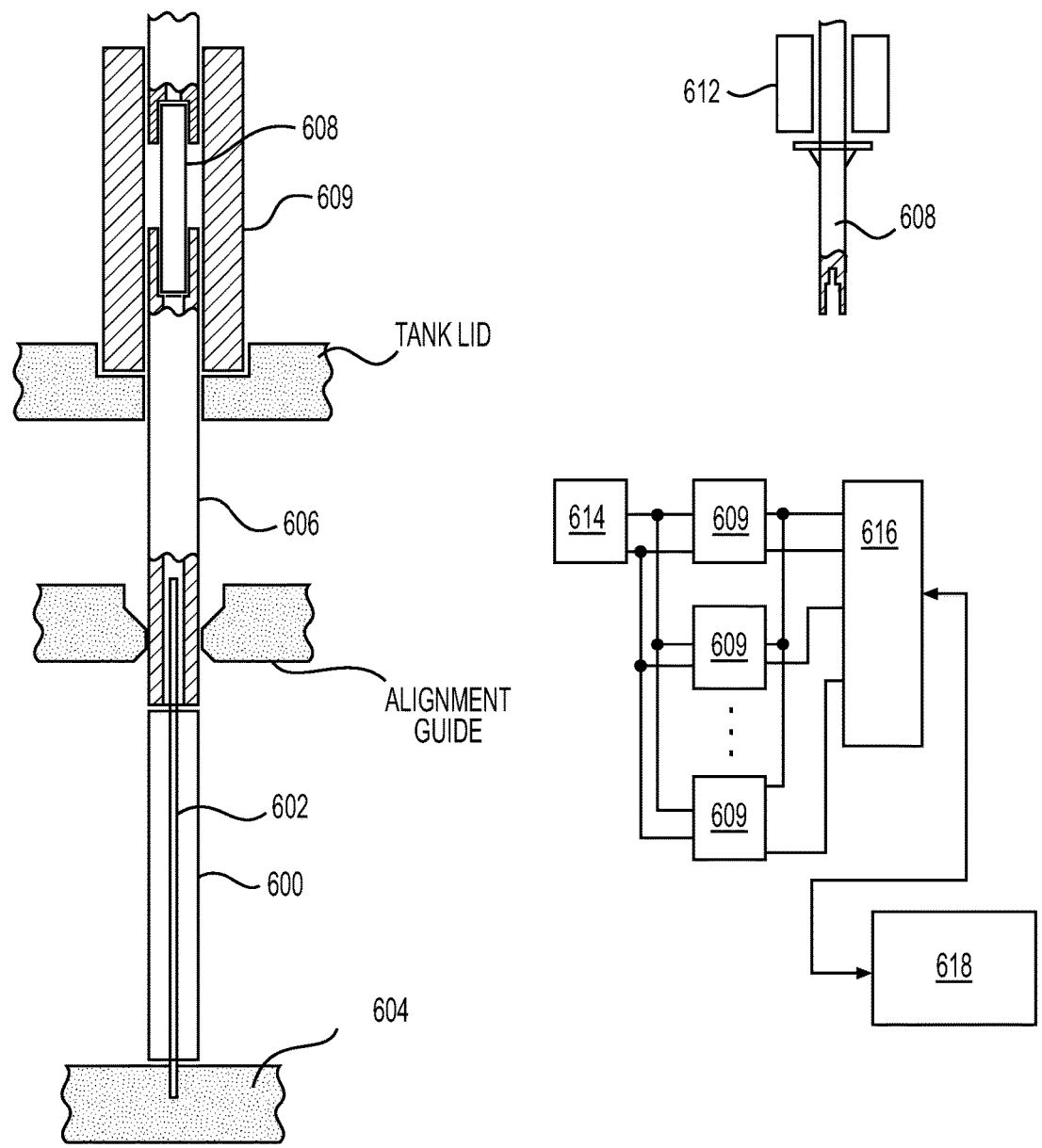
FIG. 6 illustrates a system configuration for testing various embodiments of a hose for creep.

FIG. 6 illustrates a system configuration for testing various embodiments of a hose for creep. The test comprises a water tank where the test specimen (hose 600) is placed and held in alignment on a mandrel 602 that is attached to the base 604 of the water tank. The water is heated and a compression rod 606 is applied over the test specimen/hose 600 to allow loading. A core 609 of a linear variable differential transformer (LVDT) 609 is integrated into the compression rod to allow position measurement using an LVDT. As shown in FIG. 6, the load rod 610, core 608, and compression rod assembly are referred to herein as the "compression rod" 606. A weight stack 612 is then applied to compression rod. Any creep in the hose is measured by the windings of the LVDT 609 that is positioned about the core 608. Multiple specimens may be tested concurrently in the same water tank using additional test cells.

The electrical schematic for a test system for multiple specimens is also shown in FIG. 6. In an exemplary configuration, the power supply (PS) 614 can be a TekPower™ HY 1803D set to 14.9 volts. The data acquisition module (DAQ) 616 can be a National Instruments™ USB-6008, the computer 618 can be a laptop Dell™ M4300 running Windows™ XP 5.1, service pack 2. The heater for heating the water in the tank (not shown) can be an IR009384 VWR, model 1122S. The scale for measuring the weight stack and rod weight (not shown) can be an Ohaus Adventurer™ model AR3130. The LVDT 609 and LVDT core 608 for measuring position can be Transtek models C005-0023 and 0243-00000, respectively. Data can be collected using software such as Dasy Lab from National Instruments, version 10.00.01.

Testing was performed on several samples of hose, both raw and after e-beam sterilization of the hose. The testing was conducted at 37° C., 50° C. and 60° C. The higher temperatures are used to accelerate creep that would be experienced at 37° C. (see, for example, ASTM D 2990, "Standard Test Methods for Tensile, Compressive, and Flexural Creep and Creep-Rupture of Plastics," which is incorporated by reference. Specifically, Appendix X5 of the ASTM D 2990 standard discusses acceleration of creep at higher temperatures.)

Figure 7:
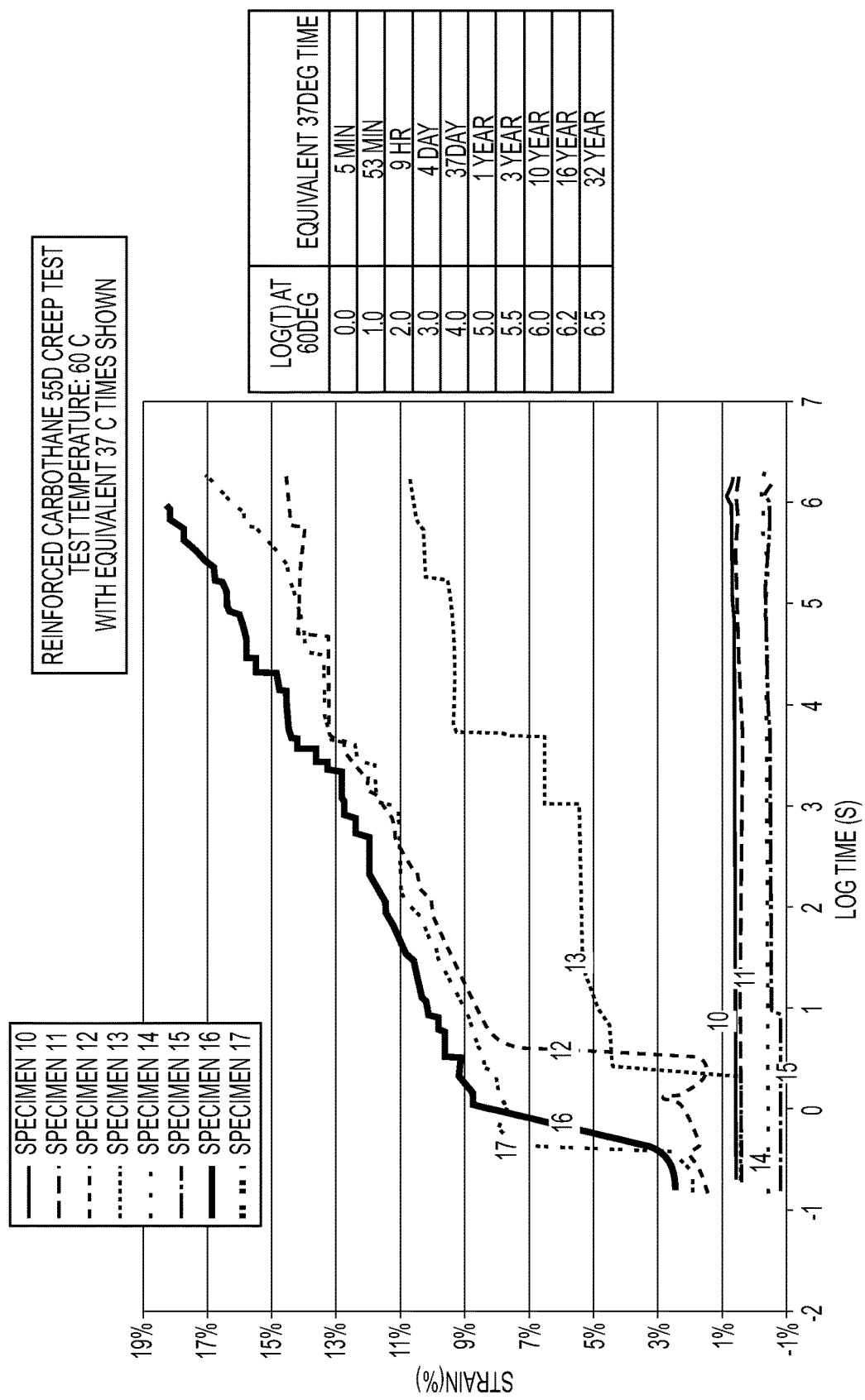
FIG. 7 illustrates the results of the testing.

FIG. 7 illustrates the results of the testing. In all instances in FIG. 7, the polymer used was Carbothane™ 55D. All samples were e-beamed for sterilization. The test temperature was 60° C., which aged the hose for equivalent 37° C. time as shown in the lower right-hand box of FIG. 7. Samples 10 and 11 comprise a hose having a first layer of polymer that forms the inner diameter; a second layer braided substantially about the first layer, wherein the second braided layer extends along the entire length of the specimen and has a pitch of 15 ppi; a third helically coiled layer substantially about the braided layer, wherein the third helically coiled layer extends along the entire length of the specimen; and a fourth layer of polymer forming the outer diameter. Samples 12 and 13 comprise a hose having a first layer of polymer that forms the inner diameter; a helically coiled layer substantially about the first layer, wherein the helically coiled layer extends along the entire length of the specimen; and a third layer of polymer forming the outer diameter. Samples 14 and 15 comprise a hose having a first layer of polymer that forms the inner diameter; a second layer braided substantially about the first layer, wherein the second braided layer extends along the entire length of the specimen and has a pitch of 30 ppi; a third helically coiled layer substantially about the braided layer, wherein the third helically coiled layer extends along the entire length of the specimen; and a third layer of polymer forming the outer diameter. Samples 16 and 17 comprise a hose having a first layer of polymer that forms the inner diameter; a second layer braided substantially about the first layer, wherein the second braided layer extends along the entire length of the specimen; and a third layer of polymer forming the outer diameter.

As can be seen in FIG. 7, the samples having the coil over braid construction (samples 10, 11, 14 and 15) have practically negligible creep and any creep that was measured was thought to be drift of the power supply rather than actual creep. Samples 16 and 17, having only the braid, experienced the largest amount of creep during the testing.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain. It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A hose, wherein said hose has a length having a distal end and a proximal end, an inner diameter and an outer diameter, said hose comprising:
    a first layer that forms the inner diameter;
    a second layer braided substantially about the first layer, wherein the second braided layer extends along at least a portion of the length;
    a third helically coiled layer substantially about the braided layer, wherein the third helically coiled layer extends along at least a portion of the length;
    a fourth layer substantially about the helically coiled layer, wherein said fourth layer forms the outer diameter; and
    a fifth layer, wherein the fifth layer is located between the second layer braided substantially about the first layer and the third helically coiled layer, wherein the material that comprises the fifth layer has a density greater than the material that comprises the first layer and the material that comprises the fourth layer.

2. The hose of claim 1, wherein the length is 850 to 975 mm.

3. The hose of claim 1, wherein the inner diameter of the hose is less than or equal to 2 mm.

4. The hose of claim 1, wherein the outer diameter of the hose is less than or equal to 5 mm.

5. The hose of claim 1, wherein a longitudinal compressive force applied to either the distal end or the proximal end causes the braided layer to lock against the helically coiled layer.

6. The hose of claim 1, wherein the second braided layer comprises a wire braided layer.

7. The hose of claim 6, wherein the wire braided layer comprises stainless steel.

8. The hose of claim 1, wherein the third helically coiled layer about the second braided layer comprises a wire helically coiled layer about the braided layer.

9. The hose of claim 1, wherein the third helically coiled layer about the second braided layer comprises a short-pitch helically coiled layer about the second braided layer.

10. The hose of claim 1, wherein a composition of the material that comprises the first layer or the fourth layer varies along the length of the hose.

11. The hose of claim 1, wherein the third helically coiled layer comprises ultra-high-molecular-weight polyethylene, glass fiber, or carbon fiber.

12. The hose of claim 1, wherein the first layer comprises a polymer.

13. The hose of claim 1, wherein the length of the hose is from 1 and 1000 mm, and the outer diameter is 5 mm or less.

14. A method of positioning a medical device in a patient using a hose, comprising:
    assembling a medical device at a distal end of a hose, wherein the hose has a proximal end and a length between the distal end and the proximal end;

delivering a flexible guideshaft via a catheter and anchoring the guideshaft at a distal location in a patient;

delivering and positioning the medical device by advancing the hose over the flexible guideshaft; and anchoring the hose at its proximal end, wherein the hose is comprised of a first layer that forms an inner diameter of the hose; a second layer braided substantially about the first layer, wherein the second braided layer extends along at least a portion of the length; a third helically coiled layer substantially about the braided layer, wherein the third helically coiled layer extends along at least a portion of the length;

a fourth layer substantially about the helically coiled layer, wherein said fourth layer forms an outer diameter of the hose; and a fifth layer, wherein the fifth layer is located between the second layer braided substantially about the first layer and the third helically coiled layer, wherein the material that comprises the fifth layer has a density greater than the material that comprises the first layer and the material that comprises the fourth layer.

15. The method of claim 14, wherein a longitudinal compressive force applied to either the distal end or the proximal end of the hose causes the second braided layer to lock against the third helically coiled layer.

16. The hose of claim 14, wherein the inner diameter of the hose is less than or equal to 2 mm.

17. The hose of claim 14, wherein the outer diameter of the hose is less than or equal to 5 mm.

18. The hose of claim 14, wherein the length of the hose is between 1 and 1000 mm.

\* \* \* \* \*